United States Patent
Lanier

(10) Patent No.: US 12,083,078 B2
(45) Date of Patent: Sep. 10, 2024

(54) PARENTERAL CANNABINOID FORMULATIONS AND USES THEREOF

(71) Applicant: Isosceles Pharmaceuticals, Inc., Wilmington, NC (US)

(72) Inventor: Brett Jackson Lanier, Wilmington, NC (US)

(73) Assignee: Isosceles Pharmaceuticals, Inc., Wilmington, NC (US)

( * ) Notice: Subject to any disclaimer, the term of this patent is extended or adjusted under 35 U.S.C. 154(b) by 0 days.

(21) Appl. No.: 17/556,098

(22) Filed: Dec. 20, 2021

(65) Prior Publication Data

US 2022/0193004 A1    Jun. 23, 2022

Related U.S. Application Data

(60) Provisional application No. 63/128,447, filed on Dec. 21, 2020.

(51) Int. Cl.
| | |
|---|---|
| *A61K 31/05* | (2006.01) |
| *A61K 47/18* | (2017.01) |
| *A61K 47/22* | (2006.01) |

(52) U.S. Cl.
CPC ............ *A61K 31/05* (2013.01); *A61K 47/183* (2013.01); *A61K 47/22* (2013.01)

(58) Field of Classification Search
CPC ...... A61K 31/05; A61K 47/183; A61K 47/22; A61K 9/0019; A61K 47/12; A61K 47/14
See application file for complete search history.

(56) References Cited

U.S. PATENT DOCUMENTS

| | | | |
|---|---|---|---|
| 10,059,683 B2 | 8/2018 | Dialer et al. | |
| 2015/0343071 A1 | 12/2015 | Vangara et al. | |
| 2016/0271252 A1 * | 9/2016 | Vangara | ............... A61K 9/08 |
| 2018/0042845 A1 * | 2/2018 | Sinai | ..................... A61K 36/185 |
| 2019/0314296 A1 * | 10/2019 | Wright | ................ A61K 31/352 |

FOREIGN PATENT DOCUMENTS

| | | | | |
|---|---|---|---|---|
| WO | WO-2018002636 A1 * | 1/2018 | ............ | A61K 31/05 |
| WO | 2020/051371 A2 | 3/2020 | | |
| WO | 2022/140245 A1 | 6/2022 | | |

OTHER PUBLICATIONS

Ewout J. Hoorn, Intravenous fluids: balancing solutions, Nov. 29, 2016, J. Nephrol, 30, 485-492 (Year: 2017).*
Millar. Front. Pharmacol. 2018, vol. 9, Art. 1365 (Year: 2018).*
International Search Report and Written Opinion for International Application No. PCT/US2021/064325, dated Mar. 16, 2022.

* cited by examiner

*Primary Examiner* — Susanna Moore
*Assistant Examiner* — Luisalberto Gonzalez
(74) *Attorney, Agent, or Firm* — DLA PIPER LLP (US); Dennis J. Parad

(57) ABSTRACT

Provided herein are non-toxic parenteral pharmaceutical formulations comprising at least one cannabinoid, typically cannabinol. The cannabinoids can be from plant sources or synthetically prepared. Methods for preparing such formulations and methods for using such formulations are also disclosed. Such methods of use include, without limitation, intravenous administration of the present formulations for the treatment of peri-operative pain. The present formulations may provide potential a replacement of, or adjuvant for dosage reduction, of opioids for acute and chronic pain management.

9 Claims, No Drawings

PARENTERAL CANNABINOID FORMULATIONS AND USES THEREOF

CROSS-REFERENCE TO RELATED APPLICATIONS

This application is related and claims priority to U.S. Provisional Patent Application Ser. No. 63/128,447 entitled "PARENTERAL CANNABINOID FORMULATIONS AND USES THEREOF" filed on Dec. 21, 2020, the application of which is hereby incorporated by reference in its entirety.

BACKGROUND

The worldwide opioid crisis is well known as reported in the media and scientific literature using statistics from well-recognized health agencies such as, for example, the World Health Organization, the United State Centers for Disease Control and the United Stated Department of Health and Human Services. Although the literature and these agencies report that the initial use of opioids occurs for a variety of reasons and sources, including voluntary use that leads to addiction, legitimate medical reasons are frequently the basis and justification for initial opioid use. The first step in medically justified opioid use, that can lead to longer-term addiction, is frequently through the use of parenterally administered opioids for peri- and/or post-operative pain. Accordingly, the pharmaceutical, health, social and medical communities have been searching, generally unsuccessfully, for alternative, effective, safe treatments for peri-operative pain management, including peri- and/or post-operative pain management.

The present invention provides certain non-toxic parenteral formulations containing one or more cannabinoid for the treatment, among other medical indications, of peri-operative pain.

Cannabinoid parenteral formulations are not commonly described in the scientific and patent literature. Generally, many of the scientific papers describe cannabinoid formulations designed for immediate injection into laboratory animals, without concern for long-term safety and/or stability. One study merely indicated formulating a cannabinoid, cannabidiol (CBD), with or without (−)-trans $\Delta^9$-tetrahydrocannabinol, solubilized in "animal fat".

A more pharmaceutically elegant parenterally-administered cannabinoid formulation has been described in U.S. Pat. Pub. 2019/0314296, which also includes a more detailed review of parenteral cannabinoid formulations developed prior to the filing date of Jun. 17, 2017 for this patent publication. The pharmaceutical formulation taught and claimed therein comprises certain key elements:
 i) a cannabinoid;
 ii) an isotonic agent;
 iii) a surfactant; and
 iv) at least one antioxidant.
The isotonic agent is defined as a group consisting of: polyethylene glycol, glycerol, saline, and glucose and are used in amounts to provide an osmolality in the range of, 100-500 mOsMol/Kg, more preferably, 200-400 mOsMol/Kg, more preferably still 285-310 mOsMol/Kg, and most preferably about 300 mOsMol/Kg. Most preferably the isotonic agent is glycerol and is present in an amount of 5 to 50 mg/ml, more preferably 10-30 mg/ml, and most preferably 20 mg/ml.

This U.S. patent application describes other potential isotonic agents for use in the described formulation such as, for example, sodium chloride (saline), dextrose (5%) and lactated Ringer's with a pH of 7.0.

Although frequently used in parenteral pharmaceutical solutions, it is well known in the pharmaceutical art that isotonic agents can be problematic and can be, in fact, toxic to a patient, particularly if the patient is also administered maintenance IV fluids. For example, the use of glucose and dextrose as IV fluids vary among countries. Without additional dextrose in a parenteral medicament, which could exacerbate the effect of the administration of IV fluids containing dextrose > [o]ne randomized trial in the peri-operative setting did show that 72% of patients receiving IV fluids containing dextrose developed transient hyperglycemia, whereas those without dextrose remained normoglycemic. Because hyperglycemia is associated with worse outcomes after acute neurological injury, dextrose may need to be avoided especially in this setting. Hoom, E. J. *Intravenous Fluids: balancing* Solutions. J Nephrol., 2020, January 28: 33(2): 387.

In addition, the use of saline (sodium chloride) has been shown to induce hyperchloremic metabolic acidosis and may impair blood coagulation. Id. It is unknown whether the addition of saline used as an isotonic agent in the formulations taught in U.S. Pat. Pub. 2019/0314296 would be toxic to patients, particularly neonates, the target patient population for the formulations taught in this patent application. However, if a neonate was also receiving IV fluids, the likelihood of saline-induced toxicity appears to be substantially increased.

As such, the use of an isotonic agent in a parenteral formulation, particularly in a parenteral cannabinoid pharmaceutical formulation, may render such formulation toxic or, at least, medically problematic, particularly when an IV solution is co-administered. Such co-administration would not be uncommon when an IV is required in addition to peri-operative pain medication.

Additionally, the referenced U.S. Patent Publication does not contain a buffer. When administered via slow infusion, there is a likelihood that pH of the administered medicament can vary and, at a likely pH of about 4.0, the patient is likely to suffer from site irritation and additional pain. A buffered cannabinoid pharmaceutical formulation would be more tolerable for the patient.

Moreover, a buffered cannabinoid parenteral formulation provides the attending physician with a known solution, particularly when other fluids and/or parenteral treatments are being administered and could be impacted by the administration, particularly by infusion, of a composition of the present invention.

Accordingly, the present invention provides a non-toxic, pharmaceutically acceptable, stable parenteral cannabinoid formulation used for, among other uses, the treatment of peri-operative pain.

SUMMARY

One aspect of the present invention provides a non-toxic parenteral pharmaceutical formulation comprising:
 i. at least one cannabinoid;
 ii. at least one surfactant;
 iii. at least one antioxidant; and
 iv. at least one chelating agent; and
 v. optionally, at least one buffering agent selected from the group consisting of hypotonic buffering agents and a hypertonic buffering agents.

Another aspect of the present invention provides a non-toxic parenteral pharmaceutical formulation comprising:
  i. at least one cannabinoid;
  ii. at least one surfactant;
  iii. at least one antioxidant and
  iv. at least one chelating agent; and
  v. optionally, at least one buffering agent selected from the group consisting of hypotonic buffering agents and a hypertonic buffering agents;
  providing an isotonic agent is not added to the formulation.

Each of the elements or constituents of the present invention are pharmaceutically acceptable.

An additional aspect provides the formulation described above wherein the cannabinoid is selected from the group consisting of at least one plant-derived cannabinoid and a synthetic cannabinoid.

A further aspect provides for the formulations described above which contains not more that 0.3% (−)-trans $\Delta^9$-tetrahydrocannabinol.

Another aspect provides for the formulations described above which is devoid of (−)-trans $\Delta^9$-tetrahydrocannabinol.

An additional aspect provides for the formulations described above which is devoid of any form of tetrahydrocannabinol, also known as "THC".

A further aspect provides the formulations described above having a shelf-life of at least twelve months without refrigeration.

An additional aspect is a formulation of the present invention that can be terminally sterilized.

Another aspect provides a method of preparing a formulation of the present invention comprising:
  i. combining at least one surfactant with an at least one antioxidant and at least one cannabinoid to a first vessel;
  ii. combining at least one of the same or different second antioxidant and at least one chelating agent to a second vessel; and
  iii. combining the contents of the first and second vessels; and
  iv. optionally adding at least one buffering agent selected from the group consisting of hypotonic buffering agents and hypertonic buffering agents.

Another aspect of the present invention provides a method of preparing a formulation of the present invention comprising:
  i. combining at least one surfactant with an at least one antioxidant and at least one cannabinoid to a first vessel;
  ii. combining at least one of the same or different second antioxidant and at least one chelating agent to a second vessel; and
  iii. combining the contents of the first and second vessels; and
  iv. optionally adding at least one buffering agent selected from the group consisting of hypotonic buffering agents and hypertonic buffering agents;
  providing an isotonic agent is not added to the formulation.

An additional aspect provides for the method described above wherein the cannabinoid is selected from the group consisting of a plant-derived cannabinoid and a synthetic cannabinoid.

A further aspect provides for the method described above wherein the formulation contains not more that 0.3% (−)-trans $\Delta^9$-tetrahydrocannabinol.

Another aspect provides for the method described above wherein the formulation is devoid of (−)-trans $\Delta^9$-tetrahydrocannabinol.

An additional aspect provides for the method described above wherein the formulation is devoid of any form of tetrahydrocannabinol, also known as "THC".

A further aspect provides for a method of treating a mammal in need of treatment comprising parenteral administration, typically intravenous administration, of a composition of the present invention. Frequently, the mammal being treated is a human.

More particularly, the present invention also provides a method of treating a mammal in need of treatment for pain selected from the group consisting of peri-operative, post-operative pain and combinations thereof comprising parenteral administration, typically intravenous administration, of a formulation of the present invention.

While the aspects of the present disclosure are susceptible to various modifications and alternative forms, specific embodiments thereof are herein described in detail. It should be understood, however, that the detailed description are not intended to limit the disclosure to the particular forms illustrated but, on the contrary, the intention is to cover all modifications, equivalents and alternatives falling within the spirit and scope of the present disclosure as defined by the appended claims. The headings used herein are used for organizational purposes only and are not meant to limit the scope of the description. As used throughout this application, the word "may" is used in a permissive sense, meaning: "having the potential to"; rather than the mandatory sense meaning: "must". Similarly, the words "include", "including" and "includes" means including, without limitation. Additionally, as used in this specification and the appended claims, the singular forms "a", "an" and "the" include singular and plural referents unless the content clearly dictates otherwise.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority hereto) to any such combinations of features. In particular, with reference to the appended claims, features from dependent claims may be combined with those of independent claims and features from respective independent claims may be combined in any appropriate manner and not merely in the specific combinations enumerated in the appended claims.

DETAILED DESCRIPTION

Definitions

The term "active pharmaceutical ingredient" means a substance or mixture of substances intended to be used in the manufacture of a drug product and that, when used in the production of a drug, becomes an active ingredient in the drug product.

The term "acute pain" as used herein means pain that has a sudden onset and commonly declines over a short time (days, hours, minutes) and may follow injury to the body and/or surgery, and which generally disappears when the bodily injury/surgical wound heals.

The term "antioxidant" has the meaning typically used in the pharmaceutical formulation arts. Exemplary anti-oxidants are described further herein.

The term "buffering agent" means a weak acid or base, typically a base as used herein, used to maintain the acidity (pH) of a solution near a chosen value after the addition of another acid or base. That is, the function of a buffering agent is to prevent a rapid change in pH when acids or bases are added to the solution. Exemplary buffering agents are described further herein.

The term "cannabinoid" means the any of a group of closely related compounds which includes, for example and without limitation, cannabichromene (CBC), cannabichromenic acid (CBCV), cannabidiol (CBD), cannabidiolic acid (CBDA), cannabidivarin (CBDV), cannabigerol (CBG), cannabigerolpropyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA) and other active constituents of the cannabis plant including, for example, each of the phytocannabinoids. Additional bioactive constituents include, for example and without limitation, cannabidiot-C1 (CBD-C1); cannabidiol-C4 (CBD-C4); and cannabidiol-C6 (CBD-C6). And bioactive metabolites such as, without limitation, 7-hydroxy. CBD. Such compounds and constituents can be derived from the cannabis plant or synthetically prepared.

The term "chelating agent" has the meaning typically used in the pharmaceutical formulation arts. Exemplary chelating agents are described further herein.

The term "chronic pain" means pain that persists past normal healing time and lacks the acute warning function of physiological nociception. Usually, pain is regarded as chronic when it lasts or recurs for more than 3 to 6 months The term "dosage form" refers to one or more vials, ampules, syringes, infusion bag or other pharmaceutically acceptable container filled with a pharmaceutical formulation solution of the present invention.

The term "peri-operative pain" refers to pain before, during, and or/after a surgical procedure.

The term "peri-operative pain management" refers to actions before, during, and/or after a surgical procedure that are intended to reduce or eliminate postoperative pain before the patient is discharged after the procedure.

The term "pharmaceutically acceptable" means that which is useful in preparing a pharmaceutical composition or formulation that is generally safe, non-toxic and neither biologically nor otherwise undesirable and includes that which is acceptable for human pharmaceutical use as well as veterinary use.

The term "surfactant" has the meaning typically used in the pharmaceutical formulation arts. As used herein, the term surfactant typically refers to the use of one or more surfactant, typically a non-ionic surfactant. Exemplary surfactants are described further herein.

The term "terminally sterilized" means, for example and without limitation, a physical method of sterilization once the formulations of the present invention are placed in a container that will be used to dispense such formulations for administration to a mammal, typically a human. Such methods include, for example, dry heat, steam, radiation and plasmas, with steam being typically used.

The term "THC" refers to a compound referred to as tetrahydrocannabinol and can include, for example, THCA, THCV, Delta-8 THC, and Delta-9 THC.

The term "treatment", or a derivative thereof, contemplates partial or complete inhibition of a targeted medical indication, frequently the treatment of pain, when a composition of the present invention is administered prophylactically or following the onset of the medical indication, particularly pain, for which such pharmaceutical formulation of the present invention is administered.

Description

The following description and examples are included to demonstrate the embodiments of the present disclosure. It should be appreciated by those of skill in the art that the pharmaceutical formulations, techniques and methods disclosed in the examples herein function in the practice of the disclosed embodiments. However, those skilled in the respective arts should, in light of the present disclosure, appreciate that changes can be made to the specific embodiments and still obtain a like or similar result without departing from the spirit and scope of the disclosed embodiments.

The present specification includes references to "one aspect/embodiment" or "an aspect/embodiment". These phrases do not necessarily refer to the same embodiment although embodiments that include any combination of the features or elements disclosed herein are generally contemplated unless expressly disclaimed herein. Particular pharmaceutical formulations, features, processes, elements or characteristics may be combined in any suitable manner consistent with this disclosure.

As referenced above, little is known regarding the formulation of a stable, non-toxic, parentally-administered cannabidiol formulation. As such, the present invention provides a non-toxic parenteral pharmaceutical formulation comprising:
  i. at least one cannabinoid;
  ii. at least one surfactant;
  iii. at least one anti-oxidant; and
  iv. at least one chelating agent; and
  v. optionally, at least one buffering agent selected from the group consisting of hypotonic buffering agents and hypertonic buffering agents.

The present invention also provides a non-toxic parenteral pharmaceutical formulation comprising:
  i. at least one cannabinoid;
  ii. at least one surfactant;
  iii. at least one anti-oxidant; and
  iv. at least one chelating agent; and
  v. optionally, at least one buffering agent selected from the group consisting of hypotonic buffering agents and a hypertonic buffering agents; providing such formulation does not include an isotonic agent.

For clarity, each of the elements or constituents of the present invention are pharmaceutically acceptable. For further clarity, the at least one antioxidant is used twice during the preparation of the formulations of the present invention, as described further hereinafter. In fact, the same or different antioxidant can be used. Accordingly, an additional aspect of the present invention provides a non-toxic parenteral pharmaceutical formulation comprising:
  i. at least one cannabinoid;
  ii. at least one surfactant;
  iii. at least two different anti-oxidants; and
  iv. at least one chelating agent; and
  v. optionally, at least one buffering agent selected from the group consisting of hypotonic buffering agents and hypertonic buffering agents.

The present invention further provides a non-toxic parenteral pharmaceutical formulation comprising:
  i. at least one cannabinoid;
  ii. at least one surfactant;

iii. at least two different anti-oxidants; and
iv. at least one chelating agent; and
v. optionally, at least one buffering agent selected from the group consisting of hypotonic buffering agents and hypertonic buffering agents; providing such formulation does not include an isotonic agent.

The at least one cannabinoid, as the active pharmaceutical ingredient, can be selected from the group consisting of, for example and without limitation, cannabichromene (CBC), cannabichromenic acid (CBCV), cannabidiol (CBD), cannabidiolic acid (CBDA), cannabidivarin (CBDV), cannabigerol (CBG), cannabigerolpropyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA) and other active constituents of the cannabis plant including, for example, each of the phytocannabinoids. Additional bioactive constituents include, for example and without limitation, cannabidiol-C1 (CBD-C1); cannabidiol-C4 (CBD-C4); and camiabidiol-C6 (CBD-C6) And bioactive metabolites such as, without limitation, 7-hydroxy CBD. Such compounds and constituents can be derived from the cannabis plant, synthetically prepared, semi-synthetically prepared or as metabolites to one or more of such cannabinoids.

In the present formulations, the most commonly used cannabinoid is cannabidiol (CBD), preferably, without any other cannabinoids. Although plant-derived CBD is acceptable for use in the present formulations, the purification methods for producing a pure or near-pure plant-derived CBD active pharmaceutical ingredient ("API") are still in the process of refinement. As such, synthetically-prepared CBD is also acceptable for use in the present formulations.

Plant-derived cannabinoids, particularly CBD, are available from a variety of United States and internationally-based suppliers that are readily identifiable through a simple interne search.

Synthetically prepared cannabidiol is a specialty chemical, available from limited producers. For example, cannabidiol API is available from Purisys LLC (Athens, Georgia, U.S.A.) and is used in the formulations described herein. Such cannabidiol can be synthetically prepared, for example and without limitation, according to the teachings set forth in U.S. Pat. No. 10,059,683 (Noramco, Inc., Wilmington, Delaware, U.S.A., Assignee) and WO2020/051371 (Noramco, Inc., Applicant). Typically, the CBD used in the present formulations is the enantiomerically pure (−)-trans CBD form.

Moreover, the cannabidiol used in the present formulation typically contains not more that 0.3% (−)-trans $\Delta^9$-tetrahydrocannabinol and, when possible, may be devoid of (−)-trans $\Delta^9$-tetrahydrocannabinol. Additionally, the cannabidiol used in the present formulation typically contains not more that 0.3% of any form of THC and, when possible, may be devoid of all forms of THC. More specifically, the API used in the present formulations contains not more than 0.3%, not more than 0.2%, not more than 0.1%, not more than 0.05%, not more than 0.01%, or any fraction thereof.

The concentration of total cannabinoid, particularly cannabidiol, used in the present formulation can vary in range including, for example and without limitation, at least 0.5 mg API per milliliter of final formulation solution. More particularly, such concentration ranges from about 0.5 to about 50 mg/mL and, more specifically, about 5 mg/mL, about 10 mg/mL, about 20 mg/mL, about 30 mg/mL, about 40 mg/mL, and about 50 mg/mL of the final formulation solution, or any fraction or whole number within the stated range.

An additional element of the present formulations is the addition of at least one pharmaceutically acceptable surfactant, typically a non-ionic surfactant. Exemplary non-ionic surfactants include, for example and without limitation, polyoxyethylene (20) sorbitan monooleate, also called polysorbate 80 (Tween® 80) which is available from a multitude of supplier including, for example, Sigma-Aldrich/MilliporeSigma, (St. Louis, Missouri U.S.A.; Tween® is a registered trademark of Croda Americas, Inc., Plainsboro, New Jersey U.S.A.); macrogol 15 hydroxystearate which is primarily a mixture of mono esters and di esters of 12-hydroxystearic acid and macrogols obtained by the ethoxylation of 12-hydroxystearic acid. The number of moles of ethylene oxide reacted per mole of 12-hydroxystearic acid is 15. Proprietary versions of these surfactants include solutol HS 15 (MedChemExpress, Monmouth Junction, New Jersey U.S.A.), and Kolliphor® HS 15 (BASF, Florham Park, New Jersey U.S.A.); and polyoxamers which are triblock copolymers of a central hydrophobic chain of polyoxypropylene flanked by two hydrophilic chains of polyoxyethylene. Polyoxamers are well known in the art and are available under the name "Pluronics®", readily supplied by a variety of suppliers found via an internet search (Pluronic® is a registered trademark of Wyandotte Chemicals Corporation, Florham Park, New Jersey U.S.A.). For the present formulations, Kolliphor® HS 15 (having a chemical name of macrogol (15) hydroxystearate or polyoxyethylated 12-hydroxystearic acid) and/or Kolliphor® ELP (having a chemical name of polyoxy-35 castor oil) is frequently used in the present formulations. Kolliphor® is a registered trademark of BASF SE, Ludwigshafen am Rein, Federal Republic of Germany.

Surfactant concentrations are used in the present formulations at a range from about 50 mg/mL to about 500 mg/mL of final formulation solution. For example, when the desired cannabinoid concentration is about 10 mg/mL of final formulation solution, the concentration of surfactant is about 150 mg/mL of final formulation solution. As the concentration of cannabinoid is increased, so is the concentration of surfactant. For further example, when the desired cannabinoid concentration is about 50 mg/mL of final formulation solution, the concentration of surfactant is about 250 mg/mL of final formulation solution. The ordinarily skilled artisan can further extrapolate the concentration of surfactant used in the present formulations based on the desired concentration of the desired at least one cannabinoid, typically cannabidiol. Additional exemplification is shown in Table 1 below.

To be more specific, the surfactant concentration in the present formulations can be about 50 mg/mL, about 100 mg/mL, about 150 mg/mL, about 200 mg/mL, about 250 mg/mL, about 300 mg/mL, about 350 mg/mL, about 400 mg/mL, about 450 mg/mL, about 500 mg/mL, or any whole or fractional number within the stated range of final formulation solution.

Antioxidants play an important role in the stability of the present formulations. During preparation of the formulations of the present invention, the same or different antioxidant is added to two separate process steps as described in more detail herein below. Generally, the process comprises a first vessel into which the at least one cannabinoid, the at least one surfactant and a first at least one antioxidant are combined; and a second vessel into which the at least one chelating agent and at least one same or different antioxidant are combined, followed by the combination of materials from the first and second vessels to provide a final formulation solution, also referred to herein as the final formulation, notwithstanding the potential addition of optional ingredients unless such ingredient or ingredients are restricted from use herein.

In the first vessel, the at least one antioxidant is added to reduce or eliminate the degradation of the at least one cannabinoid. Typically, without an antioxidant in this step, cannabidiol can rapidly degrade to a hydroxyquinone derivative, contaminating the formulation solution and reducing the desired concentration of cannabidiol in such solution formulation. The absence of a purple tint to the formulation solution is a simple test for the absence of the hydroxyquinone degradation product.

The use of the same or different one or more antioxidant added to the second vessel further stabilizes the final formulation solution, generally in aqueous form, from oxidative degradation.

Pharmaceutically acceptable antioxidants are generally known to the skilled artisan in the pharmaceutical arts and include, for example and without limitation, the following classes of antioxidants: natural antioxidants including, for example, tocopherol (Vitamin E), sesamol, guaiac resin and methionine; synthetic antioxidants including, for example, BHA, BHT, tertiary butyl hydroquinone; water-soluble antioxidant including, for example, citric acid, tartaric acid, phosphoric acid, ascorbic acid (and its precursors as delineated below), sodium metabisulfite and thiol derivatives; and oil soluble antioxidant including, for example, BHA and BHT.

For the purposes of preparing the present pharmaceutical formulations, the antioxidants used are typically selected from the group consisting of the water-soluble antioxidants. More specifically, ascorbic acid, used in the form of ascorbyl palmitate, which hydrolyses, in part or in whole depending upon the composition in which the ascorbyl acid resides, to ascorbic acid, is typically used in the first vessel. The same or different antioxidant is added to the second vessel can typically be ascorbic acid, ascorbyl palmitate, citric acid or combinations thereof although any appropriate antioxidant can be used in either the first or second vessel.

The concentration of the at least one pharmaceutically acceptable antioxidant typically comprises a total of from about 0.5 mg/mL of final formulation solution to about 10 mg/mL of final formulation solution, and more typically from about 1 mg/mL to about 5 mg/mL of final formulation solution. More specific antioxidant concentration are about 0.5 mg/mL, about 1.0 mg/mL, about 2.0 mg/mL, about 3.0 mg/mL, about 4.0 mg/mL, about 5.0 mg/mL, about 6.0 mg/mL, about 7.0 mg/mL, about 8.0 mg/mL, about 9.0 mg/mL, about 10.0 mg/mL, or any whole or fractional number within the stated range of final formulation solution. Such concentrations can be divided between the two preparatory vessels, frequently one-half of the total concentration of antioxidant in each vessel, using the same or different antioxidant in each vessel.

At least one pharmaceutically acceptable chelating agent represents an additional element of the present cannabinoid formulations of the present invention. Exemplary chelating agents include, for example and without limitation, eidetic acid (Spectrum Chemical Manufacturing Corp., New Brunswick, New Jersey U.S.A.), Versene™ NA (Dow Chemical Company, Midland, Michigan, U.S.A., and EDTA (ethylenediaminetetraacetic acid; commonly available as disodium and calcium EDTA) and the like. EDTA is readily available from a variety of sources found via a simple interne search.

The concentration of the at least one chelating agent in the present cannabinoid formulations typically is used in the range from about 0.1 mg/mL to about 5 mg/mL of final formulation solution. More specific chelating agent concentrations are about 0.1 mg/mL, 0.5 mg/mL, 1.0 mg/mL, 2.0 mg/mL, 3.0 mg/mL, 4.0 mg/mL, 5.0 mg/mL, or any whole or fractional number within the stated range of final formulation solution. Typically, the concentration of such chelating agent as used in the present formulation is from about 0.5 mg/mL to about 3.0 mg/mL of final formulation solution.

When the phrase "or any whole or fractional number within the stated range" is used herein, the phrase contemplates teaching each specific whole or fractional number not expressly stated herein. A typical dosage of a chelating agent should not exceed 50 mg/Kg of body weight, and typically, not exceed 3 gm/day. These guidances need to be considered when formulating the formulations of the present invention to avoid toxicity from the chelating agent element of the present formulations.

As referenced above, the injection site, particularly of an IV solution administered over a period of time, can cause injection site irritation and pain. A common reason for such irritation and pain is the pH of the solution being administered. Additionally, the pH of an intravenously ("IV") administered formulation of the present invention can interfere with other administered medicaments, particularly those that are IV administered. As such, a buffered cannabinoid formulation of the present invention can reduce the injection site irritation and pain, particularly when administered as an infusion, and can provide an attending physician with a known, consistent pKa of a formulation of the present invention. Moreover, buffered solutions differ from isotonic saline in terms of three properties: lower sodium and chloride contents, bringing them closer to normal plasma levels; the presence of other ions such as potassium, calcium or magnesium, which could have effects on factors such as potassium or lactate levels, or could play a role in liver disease; and their contents of anions such as lactate, acetate and gluconate, which are metabolized to bicarbonate by tissue cells and may exert an additional buffering effect. Cochrane Database Syst Rev. 2016 June; 2016(6): CD012247.

In the present formulations, the concern for the addition of an at least one optional hypotonic or hypertonic buffering agent is the maintenance of solution pH at a predetermined point rather than a targeted isotonic osmolality of the final formulation solution.

Accordingly, an optional element of the present formulations is at least one hypotonic or hypertonic buffering agent. Such buffering agents are well known in the pharmaceutical formulation development arts and include, for example and without limitation, at least one hypertonic or hypotonic (not isotonic) amount of at least one buffering agent, typically citric acid. However, other pharmaceutically acceptable buffers are known and used in liquid/aqueous pharmaceutical formulations. They include, for example and in addition to citric acid, bicarbonate buffers, carboxylic acid buffers, phosphate buffers, zwitterionic buffers, TRIS buffers and the like.

Exemplary buffers and the respective pKa offered for each such buffer:

| Buffering Agent | pKa | pH range |
|---|---|---|
| Maleic Acid | 1.9, 6.2 | 2-3 |
| Tartaric Acid | 2.9, 4.2 | 2.5-4 |
| Lactic Acid | 3.8 | 3-4.5 |
| Citric Acid | 3.1, 4.8, 6.4 | 3-7 |
| Acetic Acid | 4.75 | 4-6 |
| Sodium Bicarbonate (range) | 4.2-10.3 | 4-9 |
| Sodium Phosphate | 2.2, 7.2, 12.4 | 8-8 |

Each of such buffers, prepared to be hypotonic or hypertonic (non-isotonic), when used with the present formulations, are used in an amount required to stabilize a formulation of the present invention at a pH from about 4.5 to about pH 6.0, and more typically between pH 5.0 and pH 5.5.

Non-isotonic amounts of, for example, citric acid, are prepared by adding specific amount of citric acid to water, typically deionized water, or an aqueous solution such as the present formulations. Hypotonic or hypertonic solutions of citric acid, for example, can be readily prepared in a variety of concentrations. The amount used to buffer a formulation of the present invention will be determined by the strength of the buffer and the desired final buffered pH. Other buffers are similarly prepared and well known to the skilled artisan.

Further aspects of the present invention provide methods of preparing a formulation of the present invention:
comprising:
i. combining at least one surfactant with an at least one antioxidant and at least one cannabinoid to a first vessel;
ii. combining at least one of the same or different second antioxidant and at least one chelating agent to a second vessel; and
iii. combining the contents of the first and second vessels; and
v. optionally adding at least one buffering agent selected from the group consisting of hypotonic buffering agents and hypertonic buffering agents.

And comprising:
i. combining at least one surfactant with an at least one antioxidant and at least one cannabinoid to a first vessel;
ii. combining at least one of the same or different second antioxidant and at least one chelating agent to a second vessel; and
iii. combining the contents of the first and second vessels; and
iv. optionally adding at least one buffering agent selected from the group consisting of hypotonic buffering agents and hypertonic buffering agents;
providing an isotonic agent is not added to the formulation.

It may be possible, also, to prepare the present formulations in a one-pot process.

The following is a non-limiting and exemplary preparation of the present formulations, using two vessels for the preparation of: i) a cannabinoid, particularly synthetically-prepared cannabidiol, a surfactant and an antioxidant; and ii) an antioxidant and a chelating agent, followed by combining the solutions of the two vessels:

Preparation 1:

| Material | Amount per unit | Amount g/L | Function |
|---|---|---|---|
| Cannabidiol (CBD) | 10 mg/mL | 10.00 | Active |
| Kolliphor HS15 | 150 mg/mL (15% w/v) | 150.00 | Solubiliser |
| Citric Acid | 2 mg/mL (0.2% w/v) | 2.00 | Anti-oxidant |
| Calcium Disodium EDTA | 1 mg/mL (0.1% w/v) | 1.00 | Chelating Agent |
| Ascorbic acid | 2 mg/mL (0.2% w/v) | 2.00 | Anti-oxidant |
| Water for Injection (WFI) | Q.S to 1 mL (Q.S to 100%) | q-s to 1L | Vehicle |

1. Kolliphor HS15 was heated to about 40° C. (to allow it to become clear and molten for weighing)
2. Excess water was heated for injection to about 60° C.

Formulation:
1. 150 mg/mL (15% w/v) of Kolliphor HS15 was dispensed into Vessel A (at about 60° C.) ensuring no solidification of the Kolliphor HS15 occurred. 2 mg/mL (0.2% w/v) of citric acid was added and stirred until dissolved.
2. 10 mg/mL of CBD was slowly added to the center of Vessel A ensuring no CBD stuck to the sides of the vessel and stirred until the CBD had dissolved.

In Parallel:
3. 2.0 mg/mL (0.02% w/v) of ascorbic acid was added to Vessel B which was pre-heated to about 60° C. 25% of the final volume of pre heated water, typically "water for injection" or "WFI" was added and stirred.
4. To vessel B, 1.0 mg/mL (0.01% w/v) of calcium disodium EDTA was added and mixed until fully dissolved, then placed back in the over at about 60° C. Once Vessel A contained a clear solution with no CBD crystals present:
5. Contents from Vessel B were added to Vessel A as a slow addition while with constant stirring to prevent solidification.
6. Vessel B was rinsed with about 25% more WFI and the contents added to vessel A.
7. Water was added Q.S. to the pre-determined volume (which is the basis of the concentration of each respective element) and mixed without introduction of bubbles and air.
8. The combined solution was continued to be stirred (at about 60° C.) for about 10 minutes then left to cool to ambient temperature.

The resulting pharmaceutical formulation was used in the stability study set forth beginning in Example 1.

Generally, the present formulations are prepared as follows:

Preparation 2:
Preparation of Vessel A
HS15 must be clear and warm when dispensing.
Vessel A should be set to process condition of about 50° C. to about 70° C. The melting point of CBD is about 65 to about 71° C. CBD API particle size will impact dissolution and slight variations of heating conditions may be required for complete dissolution of the CBD API Citric acid addition to the Warm Kolliphor HS15 should prevent the solution from turning a purple color upon the addition of CBD.

Do not overheat CBD in Kolliphor HS15 as this can trigger degradation.

Preparation of Vessel B

All excipients (EDTA, Ascorbic Acid) readily dissolve in water.

Aqueous water phase is kept hot at the above-referenced temperature so that when it is added to Vessel A, solidification of Kolliphor HS15 containing CBD does not occur.

The entire process should be maintained within the temperature range set forth above.

The ascorbic acid preparation typically should not be premade.

Mixing of Phases

Addition of vessel B contents to Vessel A should be carried out slowly and mixer speed adjusted so not to create additional bubbles within the formulation.

Using a mixer or a glass rod ensures to hydrate any Kolliphor HS15 off the sides of the vessel and gets into solution the desired concentrations of each formulation element.

The solution may turn hazy as water is added; this is due to the formed micelles being larger and visible to the naked eye at elevated temperatures.

As the final formulation solution is brought to final volume, the solution will turn less hazy and typically turn completely clear when reaching ambient temperature. As such, water is added to the formulation as desired or predetermined to meet the concentration requirements set forth herein for each element of the present formulations.

Fill and Finish

Bioburden reduction

Aseptic filtration using about 0.2 micron PVDF filters or other methods known to the skilled artisan are acceptable; tubing should be platinum cured to prevent CBD adsorption onto tubing.

Typically, any bubbles are dissipated prior to filling vials or another final container for the present formulations. Filling into vials or such other containers should be conducted by weight using density of the formulation followed by an inert gas sparge to remove any dissolved oxygen.

The above allows for preparations of the present formulation using a variety of concentrations of each element, with adjustments to certain elements as the concentration of cannabinoid, typically cannabidiol, is increased. Non-limiting examples of such adjustments to the concentration of certain exemplary elements are shown in Table 1 below:

TABLE 1

| Mg/mL | Ratios Max levels of CBD and surfactant per concentration | | | | |
|---|---|---|---|---|---|
| Cannabinoid | 10 | 20 | 30 | 40 | 50 |
| HS15 Surfactant | 150 | 250 | 300 | 450 | 550 |
| Citric Acid | 2 | 2 | 4 | 4 | 4 |

The ratios for the table result in a clear liquid when Q.S. with water for injection. There is no minimum CBD concentration e.g., with 250 mg/mL the ratio of surfactant to cannabidiol is from about 0.1 to about 20 mg/mL, while maintaining stability.

Following considerable scientific development efforts, the present invention provides non-toxic formulations that are administered via at least one parenteral (intravenous (IV), intramuscular (IM) and intraperitoneal (IP) means of administration. For such means of administration, a variety of dosage forms are available. Accordingly, the present invention provides dosage forms including, for example and without limitation, one or more vials, ampules, syringes, infusion bags or other pharmaceutically acceptable containers filled with a formulation of the present invention. Such dosage forms may be single or multiple use dosage forms.

For the purpose of long-term shelf-life and stability, such dosage forms may be prepared with an inert gas headspace to assist in preventing oxidation and/or degradation of the API which is typically indicated by a change of color of the present formulations. Such inert gas can include, typically, nitrogen and argon. Moreover, longer headspace vials topped-off with such inert gas may provide additional long-term stability of the present formulations. For further protection, the glass or plastic dosage forms referenced above may by amber or dark colored to ensure against any photodegradation.

With formulations of the present invention, a given dosage form or bulk formulation can typically be maintained at ambient temperature. Such dosage forms, or bulk formulation, may also be stored under non-freezing, refrigerated conditions. The present formulations may also be freeze dried that typically requires the addition of a pharmaceutically acceptable bulking agent such as mannitol, lactose, sucrose, dextran, glycerin and/or trehalose. In lyophilized products, the bulking agents also provide cryoprotection to the product. Concentrations of added bulking agents are frequently dependent upon the nature and amount of other ingredients in the formulation. Such concentrations are known to the skilled artisan.

The present pharmaceutical formulations are stable for a period of at least six months to at least 2 years, or any whole or fractional number withing or exceeding this range. More specifically, the present formulations, in bulk form or, more particularly, in dosage form ready for use in administering the present formulations, are stable for about 6 months, about 1 year, about 1.5 years, about 2 years, or a whole or fractional number within the range of about 6 months to about 2 years, generally without refrigeration. Typically, it is desirable for the present formulation to be stable and usable for a period of at least two years following preparation of the present formulations and filled into one or more appropriate container.

Another aspect of the present invention provides a formulation of the present invention that can be terminally sterilized. Such sterilization can be completed by any method presently known or developed in the future that can provide a sterilized formulation of the present invention once such formulation is placed into a container, typically a container that will be used to dispense such formulations for administration to a mammal, typically a human. Such methods include, for example, dry heat, steam, radiation and plasmas, with steam being typically used.

Alternatively, other methods known to the skilled artisan in sterile pharmaceutical formulations can be utilized such as, for example and without limitation, gases such as ethylene oxide, glutaraldehyde, propylene oxide, hydrogen peroxide and chlorine dioxide, sterile filtration and preparation of the present formulations under aseptic manufacturing conditions such as designed with appropriate pore sizes/surface chemistries that remove bacteria and other microorganisms via size exclusion, entrapment, electrostatic attraction and other modalities.

Further, the present formulations can be compounded with other medicaments, fluids or other constituents typically used for parenteral administration.

Also provided is a cannabinol pharmaceutical formulation of the present invention prepared on or in a patch for the transdermal delivery of such pharmaceutical formulation. A wide variety of patches are known in the art and include for example, reservoir and rate-controlling membrane patches, matrix patches, active pharmaceutical ingredient in adhesive patches, electroporation, iontophoresis, sonophoresis and microneedle patches. As such, further provided is a method of delivering a pharmaceutical formulation of the present invention via one or more pharmaceutically acceptable patch delivery systems. However, present patch technologies may not be optimal for adequate delivery of the present pharmaceutical formulations requiring additional research and development to accomplish the desired dosage strength. Such patches can be used for the treatment of the disease states treatable by the parenteral formulation set forth herein and can be used as a single treatment or sequentially before, with or following one or more parenteral administrations of the parenteral pharmaceutical formulations set forth herein.

The present invention further provides a method of treating a mammal, typically a human, in need of treatment comprising parenteral administration, typically intravenous administration, of a formulation of the present invention. The medical and/or pharmaceutical use of the present formulations are not limited by exemplification as a multitude of potential medical maladies can be treated via parenteral administration, frequently via IV administration, of the formulations of the present invention.

One such use includes, for example and without limitation, parenteral admiration, typically IV administration, of a formulation of the present invention to treat pain selected from the group consisting of peri-operative pain, post-operative pain and combinations thereof or, in other words, for peri- and/or post-operative pain management. Such pain, and, thus need for treatment, can be evaluated as mild, mild to moderate, moderate, moderate to severe, severe, or other pain as described by a patient in need of treatment on any one of various pain scales used by the medical community.

Pain rating scales are used in daily clinical practice to measure pain intensity. The commonly used measurement scales include the Visual Analog Scale (VAS), the Graphic Rating Scale (GRS), the Simple Descriptor Scale (SDS), the Numerical Rating Scale (NRS), and the Faces Rating Scale (FRS). All of these scales have been documented as being valid measures of pain intensity. The three scales most commonly used in the U.S. are the numerical, word and faces scales.

The present formulations can be used, for example, to treat acute or chronic pain, including, for example, neuropathic pain and/or pain associated with certain forms of cancer, whether pari-operative pain or otherwise, in a hospital, clinic, home, military or other setting when administered and monitored by appropriate, typically, medical, personnel. Moreover, it is contemplated that the present formulations can be used to treat pain as described within the pain matrix (also known as the neuromatrix) including, for example and without limitation, pain associated with a variety of different pain syndromes including such conditions as fibromyalgia, phantom limb pain, post-herpetic neuralgia, complex regional pain syndromes (CRPS), diabetic neuropathy, and central pain related to stroke or spinal cord injuries. The methods of using the present formulations further include, for example, the treatment of pain in soft and boney tissues, pain related to trauma and, generally, any form of pain for which opioid drugs are presently used whether administered orally or via parenteral administration. The present formulations, particularly when administered as infusions, may also be used in special occasions for the treatment of severe depression and refractory headaches. The formulations of the present invention can also be used to treat Dravet Syndrome, Lennox Gastaut Syndrome, myoclonic seizures, juvenile myoclonic epilepsy, refractory epilepsy, schizophrenia, juvenile spasms, West syndrome, tuberous sclerosis complex, brain tumors, cannabis use disorder, post-traumatic stress disorder, anxiety, early psychosis, neurodegenerative diseases such as Alzheimer's Disease and Parkinsonism, and autism. More particularly, the epilepsy uses of the present pharmaceutical formulations are typically used for emergency use. Other disease states that can potentially be treated by formulations of the present invention include, for example, inflammatory diseases including cardiac inflammatory diseases such as pericarditis and endocarditis, high blood pressure and other disease states treated by a vasorelaxant, arrythmia, congestive heart failure, arterial plaque (and the reduction thereof), reducing glucose absorption from arterial walls, inhibiting endotoxin production, stroke (pre-, during and post- a stroke occurrence and, generally, by providing cerebroprotection and cerebrorecovery; treatment of ischemic and hemorrhagic stroke). The formulations of the present invention can also be used, generally, as an anti-oxidant.

The present formulations can be prepared in a variety of dosage forms include, for example, vials, ampules, syringes, infusion bag or other pharmaceutically acceptable container. Such dosage forms can be filled with one of a variety of dosage concentrations of cannabinoid, typically cannabidiol, as used in the present formulations. For example, and without limitation, such dosage forms are filled with a formulation of the present invention comprising at least 0.5 mg cannabinoid, typically cannabidiol, per milliliter of final formulation solution. More particularly, such concentration ranges from about 0.5 mg/mL to about 50 mg/mL and, more specifically, about 5 mg/mL, about 10 mg/mL, about 20 mg/mL, about 30 mg/mL, about 40 mg/mL and about 50 mg/mL of the final formulation solution, or any fraction or whole number within the stated range.

Certain dosage forms, such as, for example, syringes, containing the present formulations can be directly administered or injected into a bolus or infusion bag containing any one of a multitude of pharmaceutically acceptable fluids that may be administered to a patient. Such fluids can include, for example and without limitation, nutrients, hydrating fluids and/or other treatments for pain, other maladies and/or any other medical purposes. As a precaution, a small amount of the present formulation should be premixed with the other such fluid or fluids to ensure compatibility of the mixture prior to administration. Formulations of the present invention can be presented in other pharmaceutically acceptable containers that can be used to prepare final forms for bolus or infusion administration, frequently slow infusion over a period of time.

For use of the present formulations to treat a mammal in need of treatment relative to peri- and/or post-operative pain, such formulation is typically administered in one to two doses pre-operatively, and another one to two doses post-operatively. The actual number of doses, dosage concentration and timing of doses, is typically left to the discretion of the attending physician, physician assistant, medic and the like. Accordingly, the dosage amount, number of doses and timing of such doses is not intended to be limited by the present disclosure.

Dosages of the present formulation should be calculated on the amount of API, typically cannabidiol, on a mg/Kg basis wherein such dosage should be in the range of about 0.1 mg/Kg to about 10 mg/Kg. More particularly, such dosages include, for example, 0.1 mg/Kg, 0.5 mg/Kg, 1.0 mg/Kg, 2.0 mg/Kg, 3.0 mg/Kg, 4.0 mg/Kg, 5.0 mg/Kg, 6.0 mg/Kg, 7.0 mg/Kg, 8.0 mg/Kg, 9.0 mg/Kg, 10.0 mg/Kg, greater than 10.0 mg/Kg, or any other whole or fractional number within the stated range. The final determination of such dosage should be left to the discretion of an attending physician or other appropriate medical personnel.

Although specific embodiments have been described above, these embodiments are not intended to limit the scope of the present disclosure, even where only a single embodiment is described with respect to a particular feature. Examples of features provided in this disclosure are intended to be illustrative rather than restrictive unless stated otherwise. The present disclosure is intended to cover such alternatives, modifications and/or equivalents as would be apparent to a person skilled in the art having the benefit of this disclosure.

It is to be understood that the present pharmaceutical formulations are limited only to the ranges and or limitation set forth herein and not to variations within such ranges. It is also to be understood that the terminology used herein is for the purpose of describing particular embodiments only and is not intended to be limiting.

Further modifications and alternative embodiments of various aspects of the embodiments described in this disclosure will be apparent to the skilled artisan in view of the present disclosure. Elements and materials may be substituted for those illustrated and described herein, parts and processes may be reversed, and certain features of the embodiments may be utilized independently, all as would be apparent to one skilled in the art after having the benefit of the description. Changes may be made in the elements described herein without departing from the spirit and scope of the appended claims.

EXAMPLES

Example 1: Stability of Parenteral Formulation

The pharmaceutical formulation of Preparation 1 was submitted for stability studies. Materials, methods, data and analysis follow:
Analysis:
HPLC Analytical Method:

An Agilent 1200 series HPLC system consisting of a quaternary gradient pump, autosampler, column oven, and a single wavelength detector (UV-vis) was used to analyze CBD. The detector wavelength was set at 220 nm. The chromatographic separations were performed at 35° C. temperature on a Hichrom C18 reverse phase column ((150× 4.5 mm), 4.7 μm). The mobile phase was a mixture of Acetonitrile: 0.25% Acetic Acid: Methanol (75:20:5, v/v), filtered and flowing at the rate of 1 mL/min. The data was collected and analyzed.
Calibration Standard Preparation:

Stock solution (1.0 mg/mL) of CBD was prepared by dissolving 50 mg CBD in 50 mL HPLC grade methanol using a 50 mL volumetric flask. Then calibration standard solutions of 25, 50, 100, and 250 μg/mL of CBD were prepared by diluting the stock solutions into HPLC grade methanol.

Samples were prepared at a concentration of 0.1 mg/mL in methanol and injected onto the system.
Batch Details

| Product | Intravenous CBD 10 mg/mL |
|---|---|
| Batch Number | DP-001 |
| Fill Volume | 20 mL |

Stability Data and Acceptance Criteria:

| | Test | Acceptance Criteria | Initial | 25° C. ± 60% RH 4 weeks | 25° C. ± 60% RH 6 weeks | 40° C. ± 75% RH 4 weeks | 40° C. ± 75% RH 6 weeks |
|---|---|---|---|---|---|---|---|
| 1. | Appearance of solution | Clear colorless solution free from particulates | Complies | Complies | Complies | Complies | Complies |
| 2. | Appearance of packaging | Clear Glass vial | Complies | Complies | Complies | Complies | Complies |
| 3. | Cannabinoids CBD | 10 mg/mL (LC +/− 15%) Stability +/− 10% of initial | 11.3 mg/mL (113%) | 11.6 mg/mL (102.5% of initial) | 11.2 mg/mL (99.3% of initial) | 11.5 mg/mL (102% of initial) | 11.2 mg/mL (99.3% of initial) |
| 4. | ID by HPLC | Retention time of the major peak corresponds to that of CBD | Complies | Complies | Complies | Complies | Complies |
| 5. | pH | >3.5 | Complies (4.1) | Complies (4.0) | Complies (4.1) | Complies (4.1) | Complies (4.0) |

Stability Timepoints:

| Test Conditions | Time-Points Available (weeks) |
|---|---|
| 25 ± 3° C. 60% RH | 0, 4, 6 |
| 40 ± 3° C.: 75 ± 5% RH | 0, 4, 6 |

Data Review:

This stability study was conducted on 1 batch of 10 mg/mL CBD intravenous formulation. The development batch used was manufactured at a proposed clinical scale of 1 L manufactured lots. The batch was sub-divided to provide sufficient samples for the different storage conditions and time-points. A placebo was also set alongside this study if required at the timepoints.

EMA Guidance for Clinical Trials:

The shelf-life and storage conditions of the IMP should be defined based on the stability profile of the active substance and the available data on the IMP. Extrapolation may be used, provided that stability studies are conducted in parallel to the clinical studies and throughout its entire duration. Shelf life extrapolation can be made under the following conditions:

Results at long-term as well as at accelerated storage conditions are available;

No trends in stability behaviour are observed. If any observed, justification should be provided;

Depending on the data available, a fourfold extrapolation of real time data may be acceptable up to a shelf life of 12 months and an extrapolation of x+12 months for a shelf life of more than 12 months.

Overall throughout the 6 week study period to date, there has been insignificant change in CBD content or pH of the samples. These results at 6 weeks for the 40° C.±2° C./75% RH±5% RH storage condition are within specification. There has been no change to the physical appearance or color of the samples. The solution at point of manufacture was aseptically filtered using a 0.22 micron PVDF filter. There were no signs of crystallization of CBD within the solution as reflected on the assay results. All analytical results are within analytical variation.

All other results are within specification.

At the accelerated storage condition 40° C. 75% RH at the 6 week data for the batch complies with specification with no change over time.

The manufacture can take place in a single vessel using a heated jacketed mixer vessel. Weigh pre-warmed Kolliphor HS15 into a heated mixer vessel. Dispense cannabinoid and add to the HS15 within the mixer vessel whilst stirring. To the vessel add the antioxidant and continue mixing until dissolved. Using a liquid feeder, dispense the pre-warmed water phase containing the antioxidants, buffering agents and chelating agents and mix altogether within the mixer vessel. Once mixed, set the jacketed vessel to cool down to room temperature. On the outlet valve conduct a bioburden reduction filter prior to aseptic fill and nitrogen flush finish of the product.

I claim:

1. A non-toxic parenteral pharmaceutical formulation comprising:
    at least one cannabinoid;
    macrogol (15)-hydroxystearate;
    citric acid antioxidant;
    at least one chelating agent; and
    at least one buffering agent selected from the group consisting of hypotonic buffering agents and hypertonic buffering agents;
    providing such formulation does not include an isotonic agent;
    wherein the parenteral administration in intravenous administration; and
    wherein such formulation is devoid of any form of tetrahydrocannabinol.

2. A non-toxic parenteral pharmaceutical formulation comprising:
    at least one cannabinoid;
    macrogol (15)-hydroxystearate;
    citric acid antioxidant;
    at least one chelating agent; and
    at least one buffering agent selected from the group consisting of hypotonic buffering agents and hypertonic buffering agents;
    providing such formulation does not include an isotonic agent;
    wherein the parenteral administration in intravenous administration;
    wherein such formulation is devoid of any form of tetrahydrocannabinol; and
    wherein the at least one cannabinoid is synthetically-prepared cannabidiol.

3. The formulation of claim 1, further comprising an ascorbic acid antioxidant.

4. The formulation of claim 1, wherein the at least one chelating agent comprises EDTA.

5. The formulation of claim 1, wherein the at least one buffering agent comprises sodium bicarbonate.

6. The formulation of claim 1, wherein the at least one cannabinoid is cannabidiol.

7. The formulation of claim 2, further comprising an ascorbic acid antioxidant.

8. The formulation of claim 2, wherein the at least one chelating agent comprises EDTA.

9. The formulation of claim 2, wherein the at least one buffering agent comprises sodium bicarbonate.

* * * * *